United States Patent [19]

Loboda

[11] 4,130,476

[45] Dec. 19, 1978

[54] SEPARATION AND USE OF A GASEOUS STRIPPING MEDIA IN A HYDROTREATING PROCESS

[75] Inventor: Robert S. Loboda, Hacienda Heights, Calif.

[73] Assignee: UOP Inc., Des Plaines, Ill.

[21] Appl. No.: 823,774

[22] Filed: Aug. 11, 1977

Related U.S. Application Data

[63] Continuation-in-part of Ser. No. 706,858, Jul. 19, 1976, Pat. No. 4,058,452.

[51] Int. Cl.² ................. C10G 23/02; C10G 34/00
[52] U.S. Cl. .......................... 208/212; 208/254 H; 208/255; 208/342
[58] Field of Search ............... 208/212, 144, 255, 209, 208/341, 342, 346

[56] References Cited

U.S. PATENT DOCUMENTS

| 3,066,093 | 11/1962 | Ruef et al. | 208/212 |
| 3,907,669 | 9/1975 | Ward | 208/341 |
| 4,009,097 | 2/1977 | Ward | 208/341 |

Primary Examiner—George Crasanakis
Attorney, Agent, or Firm—James R. Hoatson, Jr.; John F. Spears, Jr.; William H. Page II

[57] ABSTRACT

A process for hydrotreating petroleum fractions wherein a hydrogen-rich gas stream passed through the reaction zone on a once-through basis is obtained by passing a hydrogen-containing feed gas stream through an absorber which removes light paraffins. The gas separated from the reaction zone effluent by partial condensation is passed into a stripper as the stripping media used to remove these same light paraffins from the liquid used in the absorber.

5 Claims, 1 Drawing Figure

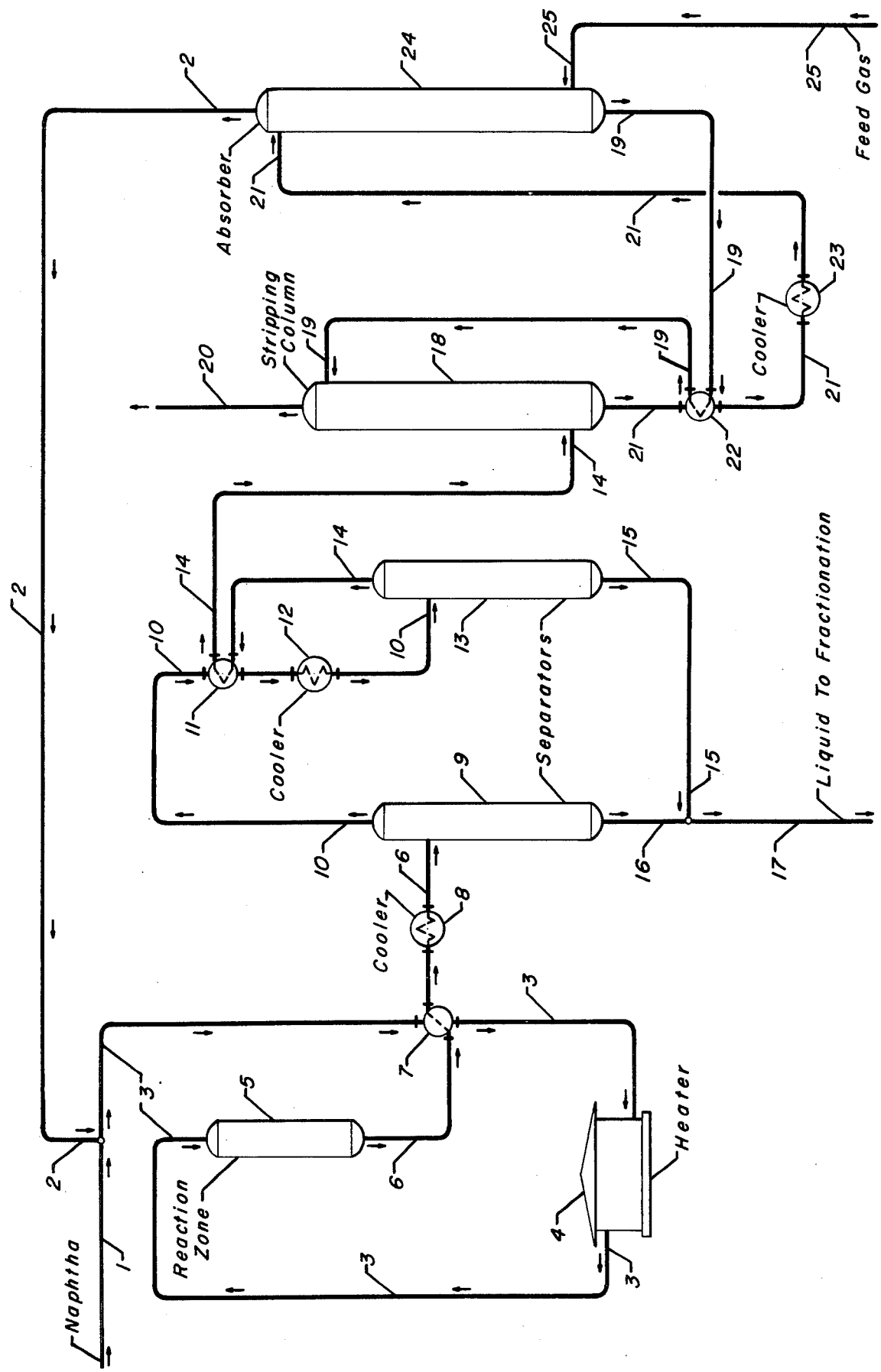

SEPARATION AND USE OF A GASEOUS STRIPPING MEDIA IN A HYDROTREATING PROCESS

CROSS-REFERENCE TO RELATED APPLICATION

This application is a continuation-in-part of my prior copending application Ser. No. 706,858, which was filed on July 19, 1976, and issued at U.S. Pat. No. 4,058,452 on Nov. 15, 1977, the teachings of which are incorporated herein by reference.

FIELD OF THE INVENTION

The invention relates to a process for the conversion of mineral oils. More specifically, the invention relates to a process for the hydrotreatment of various petroleum fractions for the removal of sulfur or nitrogen or for the saturation of olefins. The invention therefore relates to a process similar in nature to those found in Class 208 and in other classes.

PRIOR ART

Hydrotreating is widely practiced commercially. Its applications include the saturation of olefinic hydrocarbons and the desulfurization and denitrification of various petroleum fractions, such as naphthas, kerosenes or close-boiling aromatic extracts. Those skilled in the art are therefore conversant in the design, construction and operation of hydrotreating processes.

Some representative examples of the prior art of hydrotreating are provided by U.S. Pat. Nos. 3,537,982 (Cl. 208—255); 3,537,981; 3,215,618 (Cl. 208—143); 3,725,252 (Cl. 208—213); 3,700,586 (Cl. 208—89); 3,726,788 and 3,491,019. These references are relevant for their showing of representative catalyst compositions, operating conditions, feedstocks and flow schemes. They differ generally from the subject process by the use of recycle hydrogen and the lack of facilities to bypass heavier components of the hydrogen-containing makeup gas around the reaction zone.

The subject process bypasses hydrocarbons such as paraffins around the reaction zone in a manner similar to my prior copending application in which a thermal hydrodealkylation process was the preferred embodiment. It therefore seems appropriate to mention the methods in which the prior art in the field of hydrodealkylation addressed the presence of undesired hydrocarbons in the feed gas stream.

U.S. Pat. Nos. 3,284,526 and 3,291,849 present processes for the thermal dealkylation of toluene. These references recognize that charging significant quantities of paraffinic hydrocarbons, such as butane, to the reaction zone is normally undesirable. The former reference deals with this problem by operating within certain temperature and residence time limits during the reactant preheating stage. The latter reference addresses the problem in a more pertinent manner by purifying the feed hydrogen in an absorber using part of the alkylbenzene feed as the lean oil. The resulting rich oil is then passed to an appropriate unit in the refinery for fractionation. This reference differs from the subject process in several ways. One of the most basic differences is that in the subject process the paraffinic hydrocarbons which were removed from the feed gas are rejected into the effluent gas stream. Furthermore, the effluent gas stream is beneficially used in the rich oil stripper as a stripping media. In comparison, no stripper is provided in the reference, and the hydrogen vent gas is shown as being vented without utilization as the stripping media. Other differences reside in the reaction zone effluent separation method which is used and in the preferred absorber oil recycling which eliminates the need to utilize a portion of the feed stream as the lean oil.

BRIEF SUMMARY OF THE INVENTION

The invention provides a process for hydrotreating petroleum fractions in which light hydrocarbons are removed from a hydrogen-containing feed gas stream which is used on a once-through basis. The paraffinic hydrocarbons are removed from the feed gas stream in an absorber, and then the rich oil from the absorber is regenerated by stripping with the effluent gas of the process. The light hydrocarbons are thereby caused to bypass the reaction zone. The effluent gas is preferably heated for use in stripping by heat exchange in the separatory system which produces the effluent gas stream. This separatory system preferably includes two vapor-liquid separation zones with intermediate cooling. The effluent gas of the separatory system is a cold gas stream produced in the second separation zone.

DESCRIPTION OF THE DRAWING

The Drawing illustrates the preferred embodiment of the invention. For simplicity and clarity a large number of pieces of apparatus normally required to operate the process have not been shown. This apparatus includes pumps, compressors, pressure and temperature control systems, reactor and fractionator internals, etc., which may be of customary design. This depiction of the preferred embodiment is not intended to exclude from the inventive concept other embodiments set out herein or which are the result of normal and reasonable modification.

Referring now to the Drawing, a naphtha feed stream which enters the process in line 1 is admixed with a hydrogen-rich gas stream from line 2. The resultant reaction zone feed stream is passed through a heat exchanger 7 and a heater 4 by way of line 3 to raise its temperature to that desired for charging to a hydrotreating or reaction zone 5. The effluent of the reaction zone, which preferably is a vapor but may be a mixed-phase stream, is transported by line 6 through the heat exchanger 7 and a cooler 8.

The reaction zone effluent stream is then passed into a first vapor-liquid separator 9 as a mixed-phase stream. This separator is operated at conditions which promote an efficient division of the reaction zone effluent stream into a first separation zone gas stream removed in line 10 and a first condensate stream removed in line 16. The first separation zone gas stream is cooled in heat exchanger 11 and cooler 12. This forms a mixed-phase stream which is passed into a second vapor-liquid separator 13. The conditions maintained within this separator effect the separation of the entering mixed-phase stream into a second condensate stream removed in line 15 and a second separation zone gas stream removed in line 14. The first and the second condensate streams are combined and passed to a fractionation zone or other product recovery zone through line 17.

The second separation zone gas stream, which comprises hydrogen, light hydrocarbons and hydrogen sulfide or ammonia if they are formed in the reaction zone, is heated in heat exchanger 11. It is then passed into the bottom of a trayed stripping column 18 to serve as a stripping media. Additional heat may be supplied to the gas stream by a means not shown. The gas stream rises through the stripper and removes various light hydrocarbons, such as ethane, propane, butane and pentanes, from a rich oil stream fed to the top of the column in line 19. This produces an off-gas stream removed from the process in line 20. A lean oil stream is removed from the bottom of the stripping column in line 21 and cooled in heat exchanger 22 and cooler 23. The cold lead oil is then passed into the top of the trayed absorber 24. The lean oil descends the column countercurrent to a rising gas stream and removes from the gas stream the various hydrocarbons which are subsequently released in the stripping column. The feed gas stream enters the bottom of the absorber in line 25, and the portion which remains after absorption is removed in line 2 as the hydrogen-rich gas stream. A rich oil stream containing the absorbed light hydrocarbons is withdrawn from the bottom of the absorber in line 19.

DETAILED DESCRIPTION

In a great many hydrocarbon conversion processes, the hydrocarbon being processed is admixed with hydrogen prior to passage through a reaction zone. This is done for such reasons as to aid the vaporization of the hydrocarbon, to provide hydrogen which is necessary for the desired reaction or to prolong the life of the catalyst used in the reaction zone. In many cases, the hydrogen is recovered from the reaction zone effluent and recirculated. Often this recycle hydrogen stream is purified before being returned to the reaction zone. However, in a second mode of operation, referred to herein as "once-through" operation, the hydrogen is not recycled, or if recycled it is only after having passed through other processing units or purification steps. This is most commonly practiced in processes which consume only minor amounts of hydrogen or which produce hydrogen. These include isomerization processes, alkylation processes, hydrogenation processes, reforming processes and the mild desulfurization or denitrification process described herein. In its broadest embodiment, the invention is applicable to these and other processes wherein it is desired to operate with a once-through hydrogen flow.

In its preferred embodiment, the invention provides a process for the hydrotreating of various hydrocarbon feed streams, such as the saturation of olefinic hydrocarbons. These olefinic hydrocarbons may be considered impurities in the desired product. One example of this is the production of high purity paraffin mixtures. The feed stream in this specific application may be produced in a separation zone utilizing molecular sieves or solvent extraction operations which do not effect an absolute separation of paraffins and olefins having the same carbon number. Another common hydrotreating operation is the removal of sulfur- or nitrogen-containing compounds from a feed stream to a reforming or extraction unit. This results in the formation of hydrogen sulfide or ammonia, which is at least partially vented from the process in the off-gas of the stripping column.

In many instances of once-through hydrogen flow hydrotreating, it may be necessary or desirable to purify the hydrogen-containing gas stream which is fed to the process. This could be to increase the hydrogen content of the gas stream fed to the reaction zone, to increase the useful life of the catalyst or to reduce the quantity of gas which must be compressed and circulated to maintain a desired hydrogen circulation rate. It may also be desired to remove hydrocarbons which have a tendency to crack into smaller, less valuable compounds in the heater or the reaction zone. Reducing the volume of the gases in the reaction zone effluent stream may also allow a reduction in the size of the lines and vessels forming the vapor-liquid separation zone. A reduction in the volume of the gas fed to the reaction zone also reduces the duty placed on the heater and thereby reduces the utility costs of operating the process.

It is therefore an objective of this invention to provide a hydrotreating process utilizing a once-through hydrogen stream which has a lower concentration of $C_2$ to $C_5$ hydrocarbons than the feed gas stream. It is another objective of the invention to provide a once-through hydrogen flow hydrotreating process for various petroleum fractions such as napthas, gas oils, light cycle oils and other distillates or extract streams. As used herein, terms such as "naphtha" are intended to have their normal and customary meaning in the petroleum industry. For instance, naphtha is intended to refer to a mixture of hydrocarbons including paraffins and aromatics which has a boiling point range between about 90° F. and 500° F. and preferably between 100° F. and 400° F.

These and other objectives are achieved by operation in a manner similar to the preferred embodiment of the invention or the other embodiments described herein. The preferred embodiment of the invention may be characterized as a hydrotreating process which comprises the steps of passing a feed gas stream comprising hydrogen and $C_2$ to $C_4$ paraffins through an absorption zone operated under conditions effective to remove $C_2$ to $C_4$ paraffins, including countercurrent contact with a stripping zone liquid effluent stream, and thereby forming a hydrogen-rich gas stream and an absorption zone liquid effluent stream; passing the absorption zone liquid effluent stream into a stripping zone operated at conditions effective to cause the removal of $C_2$ to $C_4$ paraffins from the absorption zone liquid stream, including countercurrent contact with a gaseous stripping media, and thereby forming the stripping zone liquid effluent stream and an off-gas stream comprising hydrogen and $C_2$ to $C_4$ paraffins; admixing the hydrogen-rich gas stream with a hydrocarbon feed stream comprising $C_8$ hydrocarbons to form a reaction zone feed stream; passing the reaction zone feed stream through a catalytic hydrotreating zone and thereby forming a reaction zone effluent stream; cooling and effecting a partial condensation of the reaction zone effluent stream and passing the reaction zone effluent stream into a first vapor-liquid separation zone operated at conditions effective to form a first condensate stream and a first separation zone gas stream; passing the first condensate stream to a product recovery zone; cooling and then passing the first separation zone gas stream into a second vapor-liquid separation zone operated at conditions effective to form a second condensate stream and a second separation zone gas stream; and, heating the second separation zone gas stream by indirect heat exchange against the first separation zone gas stream and passing the second separation zone gas stream into a lower portion of the stripping zone as the gaseous stripping media.

The specific hydrocarbons which are bypassed around the reaction zone will depend on the composition of the feed gas stream. They may be a mixture of $C_2$ to $C_4$ paraffins as in the preferred embodiment. Alternatively, they may be other types of hydrocarbons, a single hydrocarbon or hydrocarbons having more than four carbon atoms per molecule. In the broad embodiment of the invention, a $C_2$ to $C_6$ hydrocarbon is bypassed around the hydrotreating zone. As in the typical absorption operation, the removal of the bypassed material will not be complete and a portion of the undesired $C_2$ to $C_6$ hydrocarbon content of the feed gas stream will remain in the gas stream which is fed to the reaction zone.

Effective conditions for the operation of the stripping zone and the absorption zone may be selected by those skilled in the art. Optimum conditions will depend on such factors as the composition of the feed gas stream, the liquid chosen for use as the absorption media and the degree of purification of the feed gas stream which is desired. A general range of conditions for the stripping zone include a pressure of from atmospheric to about 400 psig. or higher and a temperature of from about 100° F. to about 500° F. The absorption zone will be operated at a higher pressure or lower temperature or both in order to promote the absorption of the light hydrocarbons. The pressure utilized in this zone may range from about 100 psig. to 1000 psig. or higher, and the temperature may range from about 30° F. or lower to approximately 400° F. It is preferred that both zones comprise a single sieve tray contacting column, but other suitable apparatus may also be employed. The preferred absorption media comprises $C_9$-plus aromatic hydrocarbons, but any material suitable for use as a lean oil and which is readily available may be utilized.

Conditions for use in the first and second vapor-liquid separation zones will also be dependent on variable factors, such as the composition of the material being processed. It is within the expertise of those skilled in the art to select a proper set of conditions. These may be any combination of temperature, pressure and flow rate which produces an effective separation of the reaction zone effluent stream into a gaseous stream and a liquid stream of the desired hydrocarbon product. A broad range of conditions include a temperature of from about 20° F. to 300° F. or higher and a pressure of about 100 psig. to about 1500 psig. Preferably, the second separation zone is operated at a pressure which is only slightly below that utilized in the first separation zone. This allows use of the pressure differential to cause the flow of the process streams without greatly interfering with the second separation operation. The second separation zone is therefore preferably operated at a pressure within about 25 psi. of the first separation zone. The temperature of the second separation is preferably 40° to 100° F. below that used in the first separation zone. The construction of the separation zones, as well as the absorption and stripping zones, may be chosen by those skilled in the art from suitable customary designs.

The use of two vapor-liquid separation zones which are integrated as shown in the Drawing is preferred. However, the invention may be practiced with only a single vapor-liquid separation zone. The conditions used in such a system are preferably the same as those which are preferred for use in the second vapor-liquid separation zone as set out above. The overriding criteria is the production of a vapor stream suitable for use as a stripping media.

The reaction zone, also referred to herein as the hydrotreating zone, will contain a catalytically effective composite comprising an active component. This active component may be a metal or an oxide of a metal selected from Groups VIII or VI-B of the Periodic Table or a combination of these metals. The active component of the catalyst is deposited on or admixed with an inorganic oxide support such as silica or alumina. A preferred catalyst comprises nickel and cobalt on an alumina-silica support. The alumina is preferably present in greater proportions, with the weight ratio of alumina to silica being from about 1.5:1 to 9:1, and preferably 1.5:1 to 3:1. The catalyst used is subject to much variation and could be sulfided cobalt-molybdenum-alumina catalyst, etc. Other possible carrier materials include zirconia, titania, bauxite or bentonite. A commercially available catalyst may be used in the reaction zone.

Hydrotreating is normally performed at a liquid hourly spaced velocity of about 1 to 5, a pressure of about 100 to 1200 psig. and a temperature of from about 300° F. to 750° F. Hydrogen is circulated through the reaction zone at a rate of about 500 to 6,000 standard cubic feet per barrel (s.c.f./b) of feed hydrocarbons. About 200 to 1000 s.c.f./b of hydrogen is normally consumed. The severity of the hydrotreating operation will be adjusted in accordance with the specific goal of the operation, the composition of the feed stream, activity of the catalyst, etc. Further details of hydrotreating processes may be obtained by referring to such references as U.S. Pat. Nos. 3,726,788; 3,537,982 and 2,767,121.

The reaction zone may contain one or more individual reactors in parallel or in series. These reactors preferably are operated with downward flow, but may be operated with radial flow or upward flow. The reaction zone may comprise fixed bed, moving bed, ebullated bed or fluidized bed reactors.

I claim as my invention:

1. A catalytic hydrotreating process having a once-through hydrogen gas flow which comprises the steps of:

(a) passing a feed gas stream comprising hydrogen and $C_2$ to $C_4$ paraffins through an absorption zone operated under conditions effective to remove $C_2$ to $C_4$ paraffins from said gas stream, including countercurrent contact of said gas stream with a stripping zone liquid effluent stream thereby forming a hydrogen-rich gas stream and an absorption zone liquid effluent stream;

(b) passing the absorption zone liquid effluent stream into a stripping zone operated at conditions effective to cause the removal of $C_2$ to $C_4$ paraffins from said absorption zone liquid effluent stream, including countercurrent contact with a gaseous stripping media, as hereinafter delineated, thereby forming said stripping zone liquid effluent stream of step (a) and an off-gas stream comprising hydrogen and $C_2$ to $C_4$ paraffins;

(c) admixing the hydrogen-rich gas stream of step (a) with a hydrocarbon fraction to form a reaction zone feed stream;

(d) passing said reaction zone feed stream through a catalytic hydrotreating zone containing a catalyst comprising a metal or oxide of a metal selected from the group consisting of Group VIII, Group VIB, and the combination of Group VIB and Group VIII of the Periodic Table to treat said hydrocarbon with said hydrogen to form a catalytic hydrotreating reaction zone effluent;

(e) cooling and effecting a partial condensation of said reaction zone effluent and passing said effluent into a first vapor-liquid separation zone operated at a temperature of from about 20° F. to 300° F. and a pressure of about 100 psig to about 1500 psig to form a first condensate stream and a first separation zone gas stream;

(f) passing said first condensate stream to a product recovery zone;

(g) cooling and then passing said first separation zone gas stream into a second vapor-liquid separation zone operated at a lower pressure within 25 psi of the pressure of said first vapor-liquid separation zone and a temperature about 40° to 100° F. below said temperature of said first-liquid separation zone to form a second condensate stream and a second separation zone gas stream;

(h) heating the second separation zone gas stream by indirect heat exchange to provide said cooling of said first separation zone gas stream in step (g) and passing said heated second separation zone gas stream into a lower porton of the stripping zone as the gaseous stripping media in step (b); and (i) passing said second condensate stream to said product recovery zone.

2. The process of claim 1 further characterized in that the hydrocarbon fraction comprises $C_8$ hydrocarbons.

3. The process of claim 2 further characterized in that olefinic hydrocarbons present in said fraction are saturated in said catalytic hydrotreating zone.

4. The process of claim 2 further characterized in that sulfur compounds in said fraction are converted to hydrogen sulfide in said catalytic hydrotreating zone.

5. The process of claim 4 wherein said fraction comprises a naphtha.

* * * * *